United States Patent

Masloboishchikova et al.

(10) Patent No.: US 6,610,195 B2
(45) Date of Patent: Aug. 26, 2003

(54) PROCESS OF PARAFFIN ISOMERIZATION AND HETEROPOLY ACIDS SUPPORTED ON INERT SUPPORTS AS ISOMERIZATION CATALYSTS

(75) Inventors: Olga V. Masloboishchikova, Moscow (RU); Aleksandr V. Ivanow, Moscow (RU); Tatjana V. Vasina, Moscow (RU); Leonid M. Kustov, Moscow (RU); Peter Lehrmann, Birkerod (DK); Simon Jacobsen, Copenhagen D (DK); Jindrich Houzvicka, Holte (DK)

(73) Assignee: Haldor Topsoe A/S, Lyngby (DK)

( * ) Notice: Subject to any disclaimer, the term of this patent is extended or adjusted under 35 U.S.C. 154(b) by 0 days.

(21) Appl. No.: 09/902,780

(22) Filed: Jul. 12, 2001

(65) Prior Publication Data

US 2002/0023859 A1 Feb. 28, 2002

Related U.S. Application Data

(60) Provisional application No. 60/218,199, filed on Jul. 14, 2000.

(51) Int. Cl.⁷ .............................................. C10G 35/06
(52) U.S. Cl. ....................... 208/137; 208/136; 208/138; 208/139; 502/60
(58) Field of Search ................................. 208/136, 137, 208/138, 109; 502/60

(56) References Cited

U.S. PATENT DOCUMENTS 5,366,945 A * 11/1994 Kresge et al. .............. 423/277

FOREIGN PATENT DOCUMENTS

| EP | 0 623 386 A2 | 11/1994 |
| EP | 1 063 012 A1 | 12/2002 |

* cited by examiner

Primary Examiner—Walter D. Griffin
Assistant Examiner—James Arnold, Jr.
(74) Attorney, Agent, or Firm—Dickstein Shapiro Morin & Oshinsky LLP

(57) ABSTRACT

A process for conversion of hydrocarbon feed by contacting the feed with a catalyst containing heteropoly acid supported on a carrier at reaction conditions being effective in the conversion of the feed, wherein the carrier is selected from substantially inert inorganic amorphous or crystalline material, which retains characteristic structure of the heteropoly acid as evidenced by vibration frequencies around 985 and 1008 $cm^{-1}$, and which has a surface area larger than 15 $m^2/g$ excluding surface area in pores below 15 Å in diameter.

10 Claims, No Drawings

PROCESS OF PARAFFIN ISOMERIZATION AND HETEROPOLY ACIDS SUPPORTED ON INERT SUPPORTS AS ISOMERIZATION CATALYSTS

This application claims the benefit of U.S. Provisional Application No. 60/218,199, filed Jul. 14, 2000.

BACKGROUND OF THE INVENTION

The present invention is directed to hydrocarbon conversion processes by use of supported heteropoly acids as catalysts. In particular, the invention relates to isomerisation of $C_4$–$C_{24}$ paraffinic hydrocarbons.

Paraffin isomerisation is a widely used petrochemical process, which is applied mainly for increasing octane number of the $C_5/C_6$ alkane fraction in the products of crude oil processing. It is also applied, for example, in preparation of a feedstock for alkylation, e.g. butane isomerisation, in dewaxing of lube oils or in decreasing the boiling point or pour point of diesel fractions.

DETAILED DESCRIPTION OF THE INVENTION

The invention is a process for conversion of hydrocarbon feed by contacting the feed with a catalyst containing heteropoly acid supported on a carrier at reaction conditions being effective in the conversion of the feed, wherein the carrier is selected from substantially inert inorganic amorphous or crystalline material, which retains characteristic structure of the heteropoly acid as evidenced by vibration frequencies around 985 and 1008 $cm^{-1}$, and which has a surface area larger than 15 $m^2/g$ excluding surface area in pores below 15 Å in diameter.

The term heteropoly acid as used herein shall mean an acid, wherein two or more inorganic oxyacids are condensed together. The central elements of these compounds can be selected from the group consisting of P, Si, B, Ge, As, Se, Ti and Zr. As coordinating elements of these acids, such ions as Mo, W, V, Mn, Co, Ni, Cu, Zn and Fe may be used. An example of such an acid is a compound of the general formula: $H_3AB_{12}O_{40}$, where atom A is most preferably phosphorus and atom B can be most preferably W or Mo. Heteropoly acids being useful in the invention may further be various other heteropoly acids being effective catalysts in paraffin isomerisation and include $H_6As_2Mo_{18}O_{62}$, $H_6TeMo_6O_{24}$ etc. Also, various salts of heteropoly acids can be used, e.g. salts of Na, Cs, Ba. The salt must contain some remaining protons and must be supported on an appropriate support.

A noble metal is one or a mixture of several metals from the Group VIII of the Periodic Table. An alloy containing at least one or more noble metals is furthermore useful in the isomerisation reaction. Among the metals, Pt and Pd are most preferable. The noble metals are supported on the surface of the catalyst in such a way that its dispersion rate is as high as possible. Various compounds can be used in preparation of the catalysts, for example, chlorides, nitrates, iodides, acetylacetonates, acetates, ammonia-containing complexes or chloroplatinic acid. The metal can be introduced using conventional methods, for example cation exchange, incipient wetness impregnation, solid state exchange or CVD, co-precipitation and co-impregnation. The content of the metal of Group VIII in the present invention is preferably of between 0.01% and 30% by weight, more preferably between 0.05% and 5%, and most preferably 0.1% to 1% based on the total weight of the catalyst.

Oxide materials useful as support material have low concentration of basic sites and do not react with the supported heteropoly acid, thus keeping the structure of the acid intact. Typical and preferable examples of such supports are high surface titania or zirconia compounds. Further useful materials comprise silica, alumina, ceria, lanthana, various mixed oxides, zeolites or other molecular sieves. Various non-oxide supports are additionally useful support materials, such as active carbon or other carbon-based carriers, carbides or nitrides, for example silicon carbide.

The heteropoly acid can be supported onto the carrier in any known method including impregnation with aqueous or non-aqueous solutions. The content of the heteropoly acid on the support may vary from 1% to 50%. The preferable content is between 5% and 30%, and more preferably between 10% and 25%.

Preliminary treatment of the catalyst precursor comprising a heteropoly acid supported onto an inert carrier includes calcination in an air, oxygen, nitrogen or inert gas flow at a temperature ranging from 200° C. to 600° C., preferably from 350° C. to 500° C. The final catalyst containing a noble metal is activated at a temperature ranging from 200° C. to 600° C., preferably from 350° C. to 500° C. in an air, nitrogen or inert gas flow. The catalyst may further be reduced in a hydrogen flow at a temperature from 100° C. to 500° C., or it can be used without preliminary reduction.

The purpose of isomerisation is to obtain branched isomers for various purposes, for example, to increase the octane number of light naphtha, decrease the viscosity of long-chain paraffins, decrease boiling point of higher paraffins or to prepare branched isomers as a feedstock for further processing. Paraffin isomerisation is typically carried out in a continuous flow or in a batch-wise reactor in the presence of a catalyst and preferably in the presence of hydrogen. The reaction temperature can vary in a range 100–450° C. Temperatures out of this range can also be used, although they are less preferred. The most preferred temperatures for light naphtha isomerisation are in the range 100–250° C. The reaction pressures are typically 1–40 bar. The preferable pressures are 10–20 bar. Isomerisation proceeds in the presence of hydrogen to increase selectivity of the isomerisation products, stability of the catalyst and to decrease gas formation. The typical hydrogen: feed molar ratio is 0.1 to 10, usually from 0.5 to 2. Hydrogen can be diluted with an inert gas like nitrogen or helium. The volume hourly space velocities are typically from 0.1 to 10 $h^{-1}$ and usually from 0.5 to 3 $h^{-1}$.

Linear n-paraffin feed such as n-butane, n-pentane, n-hexane, n-heptane, n-octane and higher paraffins ($C_9$–$C_{16}$) or a mixture thereof are usual substrates in the isomerisation process. The feed can also contain other hydrocarbons, such as aromatic or naphthenic hydrocarbons, which do not interfere with the isomerisation reaction.

In order to illustrate further the invention and the advantages thereof, the following specific examples are given.

EXAMPLE 1

$TiO_2$ of the anatase modification (specific surface area, 40.9 $m^2/g$) (by Alfa) was used as a support for the preparation of an inventive catalyst containing heteropoly acid. $H_3PW_{12}O_{40}$ (20 wt %) was supported on $TiO_2$ from an aqueous solution (0.2 g HPW/ml) by step-by-step impregnation.

The impregnated support was dried at 120° C. for 2 h and then calcined at 350° C. for 4 h in an air flow. Pt (0.5 wt %) was supported from an $H_2PtCl_6$ aqueous solution by impregnation. The final catalyst, thus prepared, was dried at 120° C. for 2 h and calcined at 350° C. for 2 h in airflow. The final catalyst was placed in the catalytic reactor and used without pre-reduction.

EXAMPLE 2

A catalyst prepared according to Example 1 was used in a fixed-bed reactor for pentane isomerisation. The reaction was performed at 0.1 MPa total pressure with a space velocity LHSV=1 h$^{-1}$. Hydrogen: hydrocarbon ratio was 3:1 on volume basis. The catalyst performance is shown in Table 1.

TABLE 1

| Temperature, ° C. | Conversion, % | Selectivity, % |
|---|---|---|
| 190 | 52.8 | 99.0 |
| 210 | 70.0 | 95.3 |
| 230 | 73.1 | 84.8 |

EXAMPLE 3

A catalyst prepared according to Example 1 was tested in n-hexane isomerisation. The reaction was carried out at 0.1 MPa total pressure with the space velocity LHSV=1h$^{-1}$, hydrogen: n-hexane ratio 4:1 on the volume basis. The catalytic data are summarized in Table 2.

TABLE 2

| Temperature, ° C. | Conversion, % | Selectivity, % |
|---|---|---|
| 190 | 81.1 | 95.6 |
| 200 | 83.2 | 91.8 |
| 210 | 84.4 | 87.6 |

EXAMPLE 4

The fluorinated sample of γ-alumina (specific surface are 180 m$^2$/g, content of fluorine 3.5 wt %) was used for the preparation of the 0.5% Pt/20% H$_3$PW$_{12}$O$_{40}$/Al$_2$O$_3$-F catalyst according to the procedure described in Example 1. Thus, the prepared catalyst was tested in n-pentane isomerisation under conditions of Example 2. The catalyst performance is illustrated by the data presented in Table 3.

TABLE 3

| Temperature, ° C. | Conversion, % | Selectivity, % |
|---|---|---|
| 290 | 61.9 | 97.1 |
| 310 | 64.1 | 96.9 |
| 330 | 63.5 | 97.1 |

A catalyst, as prepared according to Example 4, was tested in n-hexane isomerisation under conditions described in Example 5. The catalyst performance is shown in Table 4.

TABLE 4

| Temperature, ° C. | Conversion, % | Selectivity, % |
|---|---|---|
| 270 | 70.7 | 98.3 |
| 290 | 75.4 | 97.5 |
| 310 | 75.6 | 96.4 |

EXAMPLE 5

0.25 g Pd(NO$_3$)$_2$ was dissolved in 50 ml of water. 3.76 g of tungstophosphorous heteropoly acid were dissolved in 50 ml of water. Both solutions were mixed together into a clear, light brown solution. 7 g of titania (Aerolyst from Degussa) was added to the solution under stirring. Water was evaporated in a rotary evaporator. The catalyst, thus prepared, was calcined spread on the aluminum foil with a heating ramp 0–350° C. in 8 h, at 350° C. for 6 h. The BET surface area of the catalyst was 40 m$^2$/g.

The catalyst was tested in a fixed-bed reactor in n-hexane isomerisation. The isomerisation reaction was performed at 0.3 Map total pressure with a space velocity LHSV=1.5 h$^{-1}$. The hydrogen: hydrocarbon ratio was 6:1 on the volume basis. The catalyst performance is shown in Table 5.

TABLE 5

| Temperature, ° C. | Conversion, % | Selectivity, % |
|---|---|---|
| 190 | 67.1 | 99.2 |
| 200 | 77.8 | 98.4 |
| 220 | 83.6 | 94.2 |

EXAMPLE 6

0.25 9 Pd(NO$_3$)$_2$ was dissolved in 50 ml of water. 3.76 g of phosphotungstic heteropoly acid were dissolved in 50 ml of water. Both solutions were mixed together into a clear, light brown solution. 7 g of silicon carbide were added to the solution under stirring. Water was evaporated in a rotary evaporator. The catalyst, thus obtained, was calcined in streaming air with a heating ramp 0–350° C. in 8 h, at 350° C. for 6 h. The BET surface area of the catalyst was 25 m$^2$/g.

The catalyst was tested in a fixed-bed reactor in n-hexane isomerisation. The reaction was performed at 0.3 MPa total pressure with a space velocity LHSV=1.5 h$^{-1}$. The hydrogen:hydrocarbon ratio was 6:1 on the volume basis. The catalyst performance is shown in Table 6.

TABLE 6

| Temperature, ° C. | Conversion, % | Selectivity, % |
|---|---|---|
| 230 | 77.0 | 95.6 |

EXAMPLE 7

Zirconia was prepared by precipitation of ZrOCl$_2$ with ammonia in water solution. After the filtration, the material was calcined at 300° C. for 3 h. 0.75 g Pd(acac)$_2$ was dissolved in 90 ml ethanol. 11.28 g of heteropoly acid were dissolved in 90 ml ethanol. Both solutions were mixed together and a clear, light solution was formed. 3 g of zirconia were added to 27.4 g of the solution. After ethanol was evaporated on rotary evaporator, the catalyst, thus prepared, was shaped into 0.3–0.7 mm pellets and calcined in streaming air with the heating ramp 0.3° C./min to 350° C. and 6 hours at 350° C.

The catalyst was used in a fixed-bed reactor in n-hexane isomerisation. The reaction was performed at 0.3 MPa total pressure with a space velocity LHSV=1.5 h$^{-1}$. The hydrogen: hydrocarbon ratio was 6:1 on the volume basis. The catalyst performance is shown in Table 7.

TABLE 7

| Temperature, °C. | Conversion, % | Selectivity, % |
|---|---|---|
| 205 | 77.4 | 98.9 |

What is claimed is:

1. A process for isomerization of a hydrocarbon feed containing paraffins comprising contacting the feed with a catalyst containing heteropoly acid supported on a carrier at reaction conditions being effective in the conversion of the feed, wherein the carrier is selected from substantially inert inorganic amorphous or crystalline material and retains vibration frequencies around 985 and 1008 $cm^{-1}$ of the supported heteropoly acid, the carrier having a surface area larger than 15 $m^2/g$ excluding surface area in pores below 15 Å in diameter, and the carrier being selected from the group consisting of titania, zirconia, silicon carbide, boron carbide, nitrides, graphite, and mixtures thereof.

2. A process according to claim 1, wherein the hydrocarbon feed comprises $C_4$–$C_{24}$ paraffins and the catalyst furthermore includes a Group VIII metal.

3. A process according to claim 2, wherein the isomerization is performed at a pressure from 1 to 60 bar, at temperatures from 100° C. to 450° C. in the presence of hydrogen at a hydrogen:hydrocarbon molar ratio of between 0.1:10 and 10:1.

4. A process according to claim 2, wherein the heteropoly acid is phosphotungstic and/or phosphomolybdic acid, the Group VIII metal is platinum and/or palladium and the carrier is titania and/or zirconia, or titania and/or zirconia-containing compositions.

5. A process according to claim 2, wherein the heteropoly acid is phosphotungstic and/or phosphomolybdic acid, the Group VIII metal is platinum and/or palladium and the carrier is selected from silicon carbide, boron carbide, nitrides and graphite.

6. A process for isomerization of a hydrocarbon feed containing paraffins comprising contacting the feed with a catalyst containing heteropoly acid supported on a carrier at reaction conditions being effective in the conversion of the feed, wherein the carrier is selected from substantially inert inorganic amorphous or crystalline material having a low concentration of basic sites so as to retain vibration frequencies around 985 and 1008 $cm^{-1}$ of the supported heteropoly acid, the carrier having a surface area larger than 15 $m^2/g$ excluding surface area in pores below 15 Å in diameter.

7. A process according to claim 6, wherein the hydrocarbon feed comprises $C_4$–$C_{24}$ paraffins and the catalyst furthermore includes a Group VIII metal.

8. A process according to claim 7, wherein the carrier is selected from the group consisting of titania, zirconia, silicon carbide, boron carbide, nitrides, graphite, and mixtures thereof.

9. A process according to claim 8, wherein the heteropoly acid is phosphotungstic and/or phosphomolybdic acid and the Group VIII metal is platinum and/or palladium.

10. A process according to claim 7, wherein the isomerization is performed at a pressure from 1 to 60 bar, at temperatures from 100° C. to 450° C. in the presence of hydrogen at a hydrogen:hydrocarbon molar ratio of between 0.1:10 and 10:1.

* * * * *